United States Patent [19]

Patrascu et al.

[11] Patent Number: 5,512,700

[45] Date of Patent: Apr. 30, 1996

[54] PROCESS FOR PURIFYING A BISPHENOL

[75] Inventors: Emil Patrascu, Stade; Karl Kraehling, Sasbach; Jochen Gressmann, Stade, all of Germany

[73] Assignee: Dow Deutschland Inc., Germany

[21] Appl. No.: 401,513

[22] Filed: Mar. 10, 1995

[30] Foreign Application Priority Data

Mar. 15, 1994 [GB] United Kingdom ............... 9405015

[51] Int. Cl.$^6$ .................................................. C07C 37/84
[52] U.S. Cl. ........................... 568/724; 568/722; 568/727; 568/749; 568/753
[58] Field of Search .................... 568/722, 724, 568/727, 749, 753

[56] References Cited

U.S. PATENT DOCUMENTS

| 3,326,986 | 6/1967 | Dugan et al. | 568/724 |
|---|---|---|---|
| 3,919,330 | 11/1975 | Kwantes et al. | 568/724 |
| 4,141,924 | 2/1979 | Sun | 568/724 |
| 4,354,046 | 10/1982 | Ladewig et al. | 568/724 |
| 4,408,087 | 10/1983 | Li | 568/724 |
| 4,461,915 | 7/1984 | Mendiratta et al. | 568/724 |
| 4,507,509 | 3/1985 | Mendiratta et al. | 568/724 |
| 4,533,764 | 8/1985 | Chang et al. | 568/724 |
| 4,740,634 | 4/1988 | Gomes de Matos et al. | 568/724 |
| 4,740,635 | 4/1988 | Gomes de Matos et al. | 568/724 |
| 4,861,919 | 8/1989 | Robbins et al. | 568/724 |
| 4,927,973 | 5/1990 | Dong et al. | 568/724 |

Primary Examiner—Werren B. Lone

[57] ABSTRACT

A process for the purification of a crude bisphenol comprises the following steps:

(1) preparing a mixture comprising from about 35 to about 70% of a crude bisphenol and from about 65 to about 30% of water, by the total weight of bisphenol and water, without addition of a substantial amount of an organic solvent or an alkaline compound, at a pressure above atmospheric and a temperature above about 100° C., (2) crystallizing bisphenol at a pressure below atmospheric, (3) separating crystalline bisphenol from the mother liquor, (4) dividing at least a portion of the mother liquor into a bisphenol-rich oil phase and a water-rich phase, (5) preparing a mixture comprising at least a portion of the bisphenol-rich oil phase, water and optionally an additional amount of crude bisphenol at a pressure above atmospheric and a temperature above about 100° C., (6) cooling the mixture and crystallizing bisphenol; and (7) separating crystalline bisphenol from the mother liquor.

20 Claims, No Drawings

PROCESS FOR PURIFYING A BISPHENOL

BACKGROUND OF THE INVENTION

The present invention relates to a process for the purification of bisphenols.

Bisphenols are valuable compounds useful in the preparation of various polymers, such as epoxy resins or polycarbonates. High quality epoxy resins, and particularly polycarbonates, require especially pure bisphenols for use in their preparation. Bisphenols are prepared according to various known processes by the condensation reaction of an aldehyde or a ketone and a stoichiometric excess of a phenol in the presence of a catalyst. These known processes produce bisphenols and certain impurities including isomers, analogs and homologs, such as 2-(2-hydroxyphenyl)-2-(4-hydroxyphenyl)propane (hereafter referred to as o,p-bisphenol isomer), 2,2,4-trimethyl-4-(4-hydroxyphenyl)chroman, trisphenol, polyphenol and unfavorably colored substances.

Numerous processes exist for the purification of bisphenols in general and particularly for the purification of 2,2-bis (4-hydroxyphenyl)-propane (hereafter referred to as bisphenol A or the p,p'-isomer).

U.S. Pat. No. 3,919,330 discloses a purification process wherein crude bisphenol A crystals are dissolved in an organic solvent. Water is then added, the solution is cooled, bisphenol A crystallizes and the crystals are then separated by filtration or centrifugation. U.S. Pat. No. 4,354,046 relates to a process for purifying bisphenol A wherein crude bisphenol A is mixed with toluene and a critical amount of water. The critical amount of water is 2–9% by weight based on the amount of crude bisphenol A. This mixture is heated to 80°–100° C. to form a single liquid phase. The liquid phase is then cooled whereby bisphenol A crystallizes. However, some of the organic solvents which have been suggested for the purification of bisphenols are inflammable or toxic.

A method which uses water as the crystallization medium for bisphenol A is disclosed in U.S. Pat. No. 3,326,986. According to this patent, crude bisphenol A is mixed with water at a ratio of 0.5 to 2.0 parts, preferably 1.0 part of water per part by weight of crude bisphenol A. The mixture is heated to a temperature of about 100° C. resulting in an aqueous phase and a liquid organic phase. The mixture is cooled slowly to crystallize bisphenol A. Any isomeric diphenols or other organic impurities remaining in the crystals are removed by washing with a chlorinated solvent, such as chloroform, methylene chloride, ethylene dichloride, propylene dichloride or chlorobenzene. However, the necessity to wash the crystalline bisphenol A with a chlorinated solvent for obtaining a sufficiently pure product is undesirable.

In order to overcome the disadvantages of the method taught in U.S. Pat. No. 3,326,986, U.S. Pat. No. 4,461,915 suggests mixing water-crystallized bisphenol A in the presence of water with a water-immiscible organic solvent, such as toluene, agitating the mixture and forming three phases in the agitated mixture. The phase containing mainly the organic solvent is removed and purified bisphenol A is recovered from the remaining two phases. However, the usage of large amounts of an organic solvent, such as toluene for purification purposes, is undesirable.

U.S. Pat. No. 4,507,509 suggests a method of purifying bisphenol A by washing solid crude bisphenol A with an aqueous alkaline solution. The concentration of the base ranges from 0.1 to 25 weight percent of the crude bisphenol A. However, the use of an alkaline solution for washing purposes may affect the quality of the purified bisphenol A.

U.S. Pat. No. 4,740,635 discloses a process for crystallizing bisphenol A wherein water is added to a mixture of a phenol-free mixture of bisphenol A, 0.5 to 15 weight percent diphenol isomers and impurities. The ratio of water to the crude bisphenol A mixture is between 1:1 and 3:1, preferably between 1.5:1 and 2.5:1. Water and the crude bisphenol A mixture are heated to a temperature of 95°–105° C. at ambient pressure to melt all the solid material. Then it is adiabatically cooled, while stirring, by reducing the pressure. The temperature is brought down to below 90° C., preferably to a temperature of from 55° to 75° C. The crystallized bisphenol A may be washed to further increase its purity. Unfortunately, the maximum purity of the crystallized bisphenol A, even after several washing operations, does not exceed 99.2%. U.S. Pat. No. 4,927,973 discloses a process for the continuous purification of crude bisphenol wherein, in a first step, a single liquid phase is formed which comprises a hot mixture of crude bisphenol and water in a weight ratio of 75–85% of crude bisphenol to 15–25% of water. In a second step, this mixture is continuously fed together with a stream of warm water to a first crystallization zone at a temperature sufficient to maintain a bisphenol-rich liquid phase, a water-rich phase and a crystalline phase comprising 70–95% of the total bisphenol in the mixture. When the mixture in the second step comprises 15–20 weight percent of bisphenol and 80–85 weight-percent of water, the temperature in the second step is 99°–101° C. The three-phase mixture is passed to a second crystallization zone operated at 85°–97° C. until 90–99% of the total bisphenol is crystallized. Bisphenol of very high purity is recovered, however, in the described process the bisphenol used as a starting material already has a high purity. The total amount of impurities less phenol according to the examples in the U.S. patent is only about 330 ppm, however, the total amount of impurities in the bisphenol prior to the purification process is only 1700 ppm. Single crystals and coarse agglomerates are said to be obtained in the process. However, the presence of coarse agglomerates is undesirable because they generally include mother liquor with impurities. Furthermore, the presence of agglomerates reduces the washing efficiency when the recovered crystals are washed.

U.S. Pat. No. 4,533,764 discloses a process for removing occluded organic solvent from bisphenol crystals. The crystals are placed in water which is maintained at a temperature of 100° C. or above to produce a molten water-bisphenol phase. According to the Examples the weight ratio between water and bisphenol A is 3.4:1 or 4:1 respectively. The water-bisphenol phase separates from the excess water, and the solvent occluded by the bisphenol crystals can diffuse into the water phase from where it can be flash distilled. After the flash distillation the temperature of the bisphenol-water phase is reduced to allow the bisphenol to separate from the water and to crystallize. The described process is very useful for removing organic solvents which can be distilled off. However, the described process is less useful for removing impurities which have a similar or higher boiling point than the desired bisphenol.

U.S. Pat. No. 4,141,924 discloses a process for purifying a crude crystalline aromatic compound, such as bisphenol A, wherein a dispersion of the liquified crude material in an aqueous liquid is formed by agitating the mixture at ambient pressure and at a temperature sufficient to melt the crude material. Agitation is then reduced to permit formation of three phases: a solid crystalline phase, an aqueous liquid phase and a mother liquor phase. According to one example, bisphenol A of high purity and a relatively high yield is obtained; however, in this example chlorobenzene is used as a solvent. The use of such an organic solvent is not very desirable.

U.S. Pat. No. 4,861,919 describes the purification of aromatic compounds, such as bisphenol A, by a countercurrent multi-stage water crystallization wherein the crystals are melted by the addition of heat and water prior to each crystallization step. The temperature in each crystallizer is selected depending on the desired purity of the compound to be crystallized. The temperature in the first crystallizer is relatively low, preferably about 70° C. Bisphenol A of a high yield, but of relatively low purity, is recovered from the first crystallizer. The obtained crystals are washed and melted at progressively higher temperatures in order to obtain a higher degree of purity. Crystals of extremely high purity may be achieved by this process. However, the process has to be conducted very carefully because the repeated melting of the crystals increases the risk of partial degradation or cracking of the product.

Due to the various disadvantages of the known processes, it is still desirable to provide a new process for the purification of a crude bisphenol.

SUMMARY OF THE INVENTION

The present invention relates to a process for the purification of a crude bisphenol which comprises the steps of:

(1) preparing a mixture comprising from about 35 to about 70 parts by weight of a crude bisphenol and from about 65 to about 30 parts by weight of water, without the addition of a substantial amount of an organic solvent or an alkaline compound, at a pressure above atmospheric and a temperature above about 100° C., (2) crystallizing bisphenol at a pressure below atmospheric, (3) separating crystalline bisphenol from the mother liquor, (4) dividing at least a portion of the mother liquor into a bisphenol-rich oil phase and a water-rich phase, (5) preparing a mixture comprising at least a portion of the bisphenol-rich oil phase, water and optionally an additional amount of crude bisphenol at a pressure above atmospheric and a temperature above about 100° C., (6) cooling the mixture and crystallizing bisphenol; and (7) separating crystalline bisphenol from the mother liquor.

DETAILED DESCRIPTION OF THE INVENTION

Crude bisphenol, which is purified according to the process of the present invention, is the reaction product of a phenolic compound with a carbonyl compound.

The phenolic compound can be any compound containing one or more hydroxyl groups linked to a carbon of the aromatic group. Suitable phenolic compounds include, for example, phenol and substituted phenols, the naphthols, phenanthrol, their homologues and analogues. Suitable phenolic compounds include those containing one or more phenolic groups in each nucleus as well as polynuclear compounds. Preferred phenolic compounds are those of Formula (I)

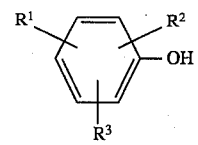

wherein: $R^1$, $R^2$ and $R^3$ independently of one another represent hydrogen, halogen, preferably chlorine or bromine, $C_{1-8}$-alkyl, $C_{5-6}$-cycloalkyl, $C_{5-10}$-aryl, preferably phenyl, or $C_{7-12}$-aralkyl, preferably phenyl$C_{1-4}$-alkyl, more preferably benzyl.

Preferred examples of the compounds of Formula (I) are phenol, cresols, xylenols, such as 2,6-dimethylphenol or 3,5-dimethylphenol, chlorophenols, dichlorophenols, 2-isopropyl-5-methyl-phenol, 5-isopropyl-2-methyl-phenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butyl-phenol, 4-methyl-2-tertiary-butylphenol, 2-tertiary-butyl-4-methylphenol, 2,3,5,6-tetramethylphenols, 2,6-ditertiary-butylphenol, 3,5-diethylphenol, 2-methyl-3,5-diethylphenol, o-phenylphenol or p-phenylphenol.

The carbonyl compound employed for producing the bisphenol can be a ketone or an aldehyde. Preferred carbonyl compounds are those of the following formula: wherein:

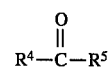

$R^4$ is an aliphatic, cycloaliphatic, aromatic or heterocyclic radical, and $R^5$ is hydrogen or an aliphatic, cycloaliphatic, aromatic or heterocyclic radical; or $R^4$ and $R^5$ together represent a divalent aliphatic or aromatic group.

Preferred groups $R^4$ and $R^5$ are $C_{1-8}$-alkyl, $C_{5-6}$-cycloalkyl, $C_{5-10}$-aryl, preferably phenyl, or $C_{7-12}$-aralkyl, preferably phenyl-$C_{1-4}$-alkyl, more preferably benzyl. These groups are optionally halogenated. When $R^4$ and $R^5$ together represent a divalent aliphatic group, the group preferably is $-(R^6CR^7)_n-$ wherein $R^6$ and $R^7$ in each occurrence individually selectable are hydrogen or $C_{1-6}$-alkyl, such as methyl or ethyl, and n is an integer from about 4 to about 7, preferably about 4 or about 5.

Examples of suitable ketones include, for example, acetone, 1,3-dichloroacetone, methyl ethyl ketone, diethyl ketone, dibutyl ketone, methyl isobutyl ketone, cyclohexanone, fluorenone, preferably 9-fluorenone, propionylphenone, methyl amyl ketone, mesityl oxide, cyclopentanone or acetophenone. Examples of suitable aldehydes include formaldehyde, acetaldehyde, propionaldehyde, butyraldehyde and benzaldehyde.

The process of the present invention is particularly suitable for the purification of bisphenol A, which is the reaction product of acetone and phenol. However, the process of the present invention is not limited thereto.

Preferably, the purity of the crude bisphenol which is further purified according to the process of the present invention is about 92% or more, more preferably about 95% or more, most preferably about 97.5% or more. Preferably the purity of the crude bisphenol is up to about 99.9%, more preferably up to about 99.7%, most preferably up to about 99.5%. Preferably, the phenol content in the crude bisphenol is not more that about 0.1%, more preferably not more than about 0.05%, based on the total weight of the crude bisphenol. The production of a crude bisphenol of such purity is well known in the art. The impurities which may be removed by the purification process of the present invention are those which are formed during the production of the desired bisphenol compound. These congeneric impurities typically include, for example, isomers and homologs of the desired bisphenol compound. For example, when bisphenol A is the desired compound, the impurities may include a variety of by-products, such as 2-(2-hydroxyphenyl)-2-(4-hydroxyphenyl)propane, 2,2,4-trimethyl-4-(4-hydroxyphenyl)chroman, trishydroxyphenyl compounds, such as 4,4'-(4-hydroxy-m-phenylenediisopropylidene)diphenyl, polyphenols, isopropenylphenol, spiro biindanes and other by-products resulting from the reaction of phenol with acetone.

In step (1) of the process of the present invention a mixture is prepared which comprises from about 35 to about 70%, preferably from about 40 to about 60%, more preferably from about 50 to about 55% of crude bisphenol and from about 30 to about 65%, preferably from about 40 to about 60%, more preferably from about 45 to about 50% of water, based on the total weight of bisphenol and water. The bisphenol can be preheated and partially or entirely molten before it is mixed with water. When bisphenol is preheated, it is preferably heated to a temperature of from about 155° to about 240° C., more preferably from about 170° to about 205° C. Water can also be preheated before it is mixed with bisphenol. When water is preheated, it is preferably heated to a temperature of from about 45° to about 105° C., more preferably from about 80° to about 99° C. The mixture is prepared at a pressure above atmospheric, preferably at a pressure of up to about 5 bar, and a temperature above about 100° C., preferably at a temperature of up to about 150° C. The preferred pressure is from about 1.5 to about 5 bar, more preferably from about 2.5 to about 5 bar, most preferably from about 3.5 to about 4 bar. The temperature preferably is from about 110° to about 150° C., more preferably from about 120° to about 130° C. Preferably, distilled or deionized water is used for preparing the mixture of crude bisphenol and water. In order to reduce the water consumption in step (1), generally up to about 90%, preferably from about 50 to about 80% of the volume of water used in step (1) may be recycled water originating from steps (4) and/or (7) described further below. No substantial amount of an organic solvent or an alkaline compound is added. This means that no more than about 5%, preferably no more than about 2%, more preferably no more than about 1% of an organic solvent is added, based on the weight of the crude bisphenol, if an organic solvent is added at all. Most preferably, no organic solvent is added. Furthermore, no more than about 0.3%, preferably no more than about 0.15%, more preferably no more than about 0.05% of an alkaline compound is added, based on the weight of the crude bisphenol, if an alkaline compound is added at all. Most preferably, no alkaline compound is added.

In step (2) of the process of the present invention the pressure is reduced to below atmospheric, preferably to an absolute pressure of from about 640 to about 920 mbar, more preferably from about 700 to about 900 mbar, most preferably from about 720 to about 860 mbar. When lowering the pressure, the hot mixture resulting from step (1) is preferably cooled to a temperature of from about 80° to about 100° C., more preferably from about 88° to about 98° C., most preferably from about 92° to about 97° C. The cooling is preferably conducted adiabatically. The freezing point of the bisphenol depends on the percentage of impurities present. The presence of the o,p-bisphenol isomer and other impurities decreases the freezing point of the composition being crystallized. At the freezing point crystalline bisphenol and two liquid phases, that is a bisphenol-rich liquid phase and a water-rich phase, coexist in equilibrium.

In step (3) of the process of the present invention crystalline bisphenol is separated from the mother liquor. The bisphenol crystals can be recovered by techniques known in the art, such as filtration or centrifugation, preferably at atmospheric pressure. The temperature in step (3) generally is from about 80° to about 110° C. preferably from about 92° to about 105° C., more preferably from about 95° to about 102° C. The recovered crystals can be washed with a washing liquor, such as water, organic solvents or mixtures of water and organic solvents. Distilled or deionized water is the preferred washing liquor. Washing with an organic solvent is not necessary. The washing liquor generally has a temperature of from about 70° to about 105° C., preferably from about 85° to about 100° C. The amount of the washing liquor preferably is from about 10 to about 80%, more preferably from about 20 to about 60%, most preferably from about 25 to about 45%, based on the weight of the bisphenol crystals.

In step (4) of the process of the present invention at least a portion of the mother liquor is divided into a bisphenol-rich oil phase and a water-rich phase. Generally at least about 50%, preferably at least about 75%, more preferably at least about 90% of the total volume and most preferably substantially the entire volume of the mother liquor is separated into two phases. The two phases can be separated by known means, such as decantation or centrifugation. The temperature in step (4) generally is from about 60° to about 105° C., preferably from about 72° to about 98° C., more preferably from about 80° to about 95° C. Step (4) is advantageously conducted at atmospheric pressure although a pressure above or below atmospheric is also useful. The resulting bisphenol-rich oil phase generally contains more than about 50%, preferably more than about 78%, more preferably more than about 94% of the total weight of bisphenol present in the mother liquor. The resulting water-rich phase generally contains more than about 50%, preferably more than about 62%, more preferably more than about 72% of the total weight of water present in the mother liquor. The entire amount or a part of the water-rich phase can be disposed of or recycled to steps (1) and/or (5).

In step (5) of the process of the present invention a mixture is prepared which comprises at least a portion of the bisphenol-rich oil phase, water and optionally an additional amount of crude bisphenol. Prior to mixing, the bisphenol-rich oil phase preferably has a temperature of from about 60° to about 105° C., more preferably from about 72° to about 98° C., most preferably from about 80° to about 95° C. Water can be preheated before it is mixed with the bisphenol-rich phase. When water is preheated, it is preferably heated to a temperature of from about 85° to about 105° C., more preferably from about 95° to about 102° C. If crude bisphenol is mixed with the bisphenol-rich oil phase, the crude bisphenol can be preheated and partially or entirely molten before it is mixed with the other components. When crude bisphenol is preheated, it is preferably heated to a temperature of from about 155° to about 240° C., more preferably from about 170° to about 205° C. Generally at least about 50%, preferably at least about 75%, more preferably at least about 90% of the total volume and most preferably substantially the entire volume of the bisphenol-rich oil phase which has been recovered in step (4) is used in step (5) of the process of the present invention. The mixture preferably comprises from about 25 to about 100, more preferably from about 25 to about 90, most preferably from about 60 to about 70 weight parts of the bisphenol-rich oil phase, from 0 to about 75, preferably from about 10 to about 75, more preferably from about 30 to about 40 weight parts of crude bisphenol and from about 65 to about 200, preferably from about 80 to about 150, more preferably from about 100 to about 125 weight parts of water. The mixture is prepared at a pressure above atmospheric, preferably at a pressure of up to about 5 bar, and a temperature above about 100° C., preferably at a temperature of up to about 150° C. The preferred pressure is from about 1.5 to about 5 bar, more preferably from about 2.1 to about 4.5 bar, most preferably from about 2.5 to about 3 bar. The temperature preferably is from about 110° to about 140° C., more preferably from about 115° to about 125° C. Preferably, distilled or deionized water is used for preparing the mixture. In order to reduce the water consumption in step (5), generally up to about 90%, preferably from about 50 to about 80% of the volume of water used in step (5) may be recycled water originating from steps (4) and/or (7). Generally no substantial amount of an organic solvent or an alkaline compound is added to the mixture. The term "no substantial amount" as used herein has the meaning as described above in step (1).

In step (6) of the process of the present invention the mixture is cooled and bisphenol A crystallizes. The mixture is preferably cooled to a temperature of from about 70° to about 98° C., more preferably from about 80° to about 95° C., most preferably from about 85° to about 92° C. The cooling is preferably conducted adiabatically. The cooling and crystallization is conducted in a crystallizer. Preferably, the pressure in the crystallizer is reduced to below atmospheric, preferably to an absolute pressure of from about 420 to about 920 mbar, more preferably from about 560 to about 900 mbar, most preferably from about 700 to about 880 mbar. The amount of impurities present in the mixture, comprising bisphenol-rich phase, water and optionally crude bisphenol, is not critical as long as the solubility of these impurities in the water is not exceeded.

In step (7) of the process of the present invention crystalline bisphenol is separated from the mother liquor. The bisphenol crystals can be recovered by techniques known in the art, such as filtration or centrifugation. The temperature and the pressure in step (7) are generally about the same as in step (3). The recovered crystals can be washed with washing liquor, such as water, organic solvents or mixtures of water and organic solvents. Distilled or deionized water is the preferred washing liquor. Washing with an organic solvent is not necessary. The washing liquor generally has a temperature of from about 70° to about 105° C., preferably from about 85° to about 100° C. The amount of the washing liquor preferably is from about 10 to about 80%, more preferably from about 20 to about 60%, most preferably from about 25 to about 45%, based on the weight of the bisphenol crystals.

The entire amount or a part of the mother liquor left after the separation of crystalline bisphenol can be disposed of or recycled to steps (1) and/or (5).

The process of the present invention is preferably conducted continuously although it can also be conducted in batches. According to the process of the present invention bisphenol of high purity and high yield is obtained. At least according to the preferred embodiments of the process of the present invention a yield of purified bisphenol of from about 82 to about 95% is achieved, based on the weight of the crude bisphenol, and the purity of the purified bisphenol generally is at least about 99.7%. Crystalline bisphenol having very large and firm crystals is obtained. The crystallization process of the bisphenol can be controlled very well. The use of an organic solvent or of an alkaline compound is not necessary in the process of the present invention. In the case of bisphenol A, the o,p-bisphenol isomer can be separated from the desired p,p-bisphenol to a very large degree. Furthermore, applicants have found that the above-mentioned advantages are even achieved when running the purification process continuously on a large scale.

A preferred embodiment of the present invention is described as follows. It is to be understood that the drawing represents only one preferred embodiment of the process of the present invention and is not to be construed as limiting the scope of the invention.

A feed stream 11 of crude bisphenol and a feed stream of water are continuously fed into a first mixer. In the first mixer, the two feed streams are mixed under conditions described above in step (1). The hot mixture is fed into a first crystallizer wherein the crystallization of bisphenol is conducted as described above in step (2). The obtained suspension is continuously fed into a separator, such as a filter, centrifuge or decanter, wherein crystalline bisphenol is separated from the mother liquor and washed as described in step (3) above. The crystalline bisphenol is removed from the separator, dried and collected in a storage device, such as a hopper. The mother liquor is removed from the separator and fed into a liquid/oil separating device wherein, in step (4), it is divided into a bisphenol-rich oil phase and a water-rich phase. The bisphenol-rich oil phase is continuously fed into a second mixer. Crude bisphenol is optionally fed and water is fed into the second mixer. The mentioned feed streams are mixed under the conditions described above in step (5). The hot mixture is fed into a second crystallizer wherein the crystallization of bisphenol is conducted as described above in step (6). The obtained suspension is continuously fed into a separator wherein crystalline bisphenol is separated from the mother liquor and washed as described in step (7) above. The crystalline bisphenol is removed from the separator, dried and collected in a storage device. The mother liquor is removed from the separator.

The present invention is further illustrated by the following example which should not be construed to limit the scope of the present invention. Unless otherwise indicated, all parts and percentages are by weight.

EXAMPLE

A feed stream of 2100 parts/hour of crude bisphenol A consisting of molten p,p-isomer of 98% purity of a temperature of 190° C. and a feed stream of 2100 parts/hour of deionized water of a temperature of 96° C. are continuously fed into a first mixer. The resulting pressure of the mixture is about 3.8 bar and the temperature about 125° C. The hot mixture is injected into a first crystallizer. It is worked adiabatically at 95° C. and an absolute pressure of 810 mbar. The obtained suspension is continuously fed into a separator wherein crystalline bisphenol is separated from the mother liquor. The bisphenol crystals are washed in the separator with hot deionized water having a temperature of 99° C. in a ratio of water:crystals of 1:3. About 1675 parts/hour of purified crystalline bisphenol are removed from the separator and after drying collected in a storage device. The crystals have an o,p-isomer concentration of less than 0.20%. The mother liquor is removed from the separator and fed into a liquid/oil separating device where it is separated into a bisphenol-rich oil phase and a water-rich phase. About 425 parts/hour of bisphenol-rich oil phase are continuously fed into a second mixer. 200 parts/hour of molten crude bisphenol A at a temperature of 190° C. are fed and 700 parts/hour of deionized water at a temperature of 96° C. are fed into the second mixer. The resulting pressure of the mixture is about 3.2 bar and the temperature about 115° C. The hot mixture is injected into a second crystallizer. It is worked adiabatically at 91° C. and an absolute pressure of 770 mbar. The obtained suspension is continuously fed into a separator wherein crystalline bisphenol is separated from the mother liquor which is removed from the separator. The bisphenol crystals are washed in the centrifuge with hot deionized water having a temperature of 99° C. in a ratio of water:crystals of 1:3. About 375 parts/hour of purified crystalline bisphenol are removed from the separator and after drying collected in a storage device. The crystals have an o,p-isomer concentration of less than 0.20%. The overall yield of the purified bisphenol A crystals, after both crystallization steps, is 89% based on the weight of the crude bisphenol A prior to purification.

What is claimed is:

1. A process for the purification of a crude bisphenol which comprises the steps of:
   (1) preparing a mixture comprising from about 35 to about 70 parts by weight of a crude bisphenol and from about 65 to about 30 parts by weight of water, without addition of a substantial amount of organic solvent or an alkaline compound, at a pressure above atmospheric and a temperature above about 100° C.,
   (2) crystallizing bisphenol at a pressure below atmospheric,
   (3) separating crystalline bisphenol from the mother liquor,
   (4) dividing at least a portion of the mother liquor into a bisphenol-rich oil phase and a water-rich phase,
   (5) preparing a mixture comprising at least a portion of the bisphenol-rich oil phase and water at a pressure above atmospheric and a temperature above about 100° C.,
   (6) cooling the mixture and crystallizing bisphenol; and
   (7) separating crystalline bisphenol from the mother liquor.

2. The process of claim 1 wherein an additional amount of crude bisphenol is included in the mixture prepared in step (5).

3. The process of claim 2 wherein the mixture prepared in step (5) comprises from about 25 to about 90 parts by weight of the bisphenol-rich oil phase and from about 75 to about 10 parts by weight of additional crude bisphenol.

4. The process of claim 3 wherein the mixture prepared in step (5) comprises from about 65 to about 200 parts by weight of water.

5. The process of claim 1 wherein the pressure in step (1) is from about 1.5 to about 5 bar.

6. The process of claim 2 wherein the pressure in step (1) is from about 1.5 to about 5 bar.

7. The process of claim 4 wherein the pressure in step (1) is from about 1.5 to about 5 bar.

8. The process of claim 1 wherein the temperature in step (1) is from about 110° C. to about 150° C.

9. The process of claim 4 wherein the temperature in step (1) is from about 110° C. to about 150° C.

10. The process of claim 1 wherein in step (2) the mixture is cooled to a temperature of from about 80° C. to about 100° C.

11. The process of claim 4 wherein in step (2) the mixture is cooled to a temperature of from about 80° C. to about 100° C.

12. The process of claim 1 wherein the pressure in step (5) is from about 2.1 to about 4.5 bar.

13. The process of claim 2 wherein the pressure in step (5) is from about 2.1 to about 4.5 bar.

14. The process of claim 4 wherein the pressure in step (5) is from about 2.1 to about 4.5 bar.

15. The process of claim 1 wherein in step (6) the mixture is cooled to a temperature of from about 70° C. to about 98° C.

16. The process of claim 4 wherein in step (6) the mixture is cooled to a temperature of from about 70° C. to about 98° C.

17. The process of claim 1 wherein in step (6) the pressure is decreased to an absolute pressure of from about 420 to about 920 mbar.

18. The process of claim 4 wherein in step (6) the pressure is decreased to an absolute pressure of from about 420 to about 920 mbar.

19. The process of claim 1 wherein separated crystalline bisphenol is washed with water at a temperature of from about 70° C. to about 100° C.

20. The process of claim 1 wherein separated crystalline bisphenol is washed with water at a temperature of from about 70° to about 100° C.

* * * * *